United States Patent
Graumann et al.

(10) Patent No.: US 9,763,599 B2
(45) Date of Patent: Sep. 19, 2017

(54) METHOD FOR REPOSITIONING A MOBILE IMAGING SYSTEM, IMAGE CAPTURING UNIT AND OPTICAL MARKER

(71) Applicant: SIEMENS AKTIENGESELLSCHAFT, Munich (DE)

(72) Inventors: Rainer Graumann, Hoechstadt (DE); Sultan Haider, Erlangen (DE); Gerhard Kleinszig, Forchheim (DE); Jessica Magaraggia, Cornedo (IT)

(73) Assignee: Siemens Aktiengesellschaft, Munich (DE)

( * ) Notice: Subject to any disclaimer, the term of this patent is extended or adjusted under 35 U.S.C. 154(b) by 13 days.

(21) Appl. No.: 14/475,758

(22) Filed: Sep. 3, 2014

(65) Prior Publication Data
US 2015/0065866 A1    Mar. 5, 2015

(30) Foreign Application Priority Data

Sep. 3, 2013 (DE) .................. 10 2013 217 476

(51) Int. Cl.
| | |
|---|---|
| *A61B 5/06* | (2006.01) |
| *A61B 5/00* | (2006.01) |
| *A61B 6/00* | (2006.01) |
| *A61B 6/08* | (2006.01) |
| *A61B 90/00* | (2016.01) |
| *A61B 6/04* | (2006.01) |

(52) U.S. Cl.
CPC ............ *A61B 5/064* (2013.01); *A61B 5/0073* (2013.01); *A61B 6/08* (2013.01); *A61B 6/4405* (2013.01); *A61B 6/547* (2013.01); *A61B 6/584* (2013.01); *A61B 90/39* (2016.02); *A61B 6/0492* (2013.01); *A61B 6/4441* (2013.01); *A61B 2090/3937* (2016.02)

(58) Field of Classification Search
CPC ......... A61B 9/54; A61B 5/0073; A61B 5/064; A61B 6/0492; A61B 6/08
See application file for complete search history.

(56) References Cited

U.S. PATENT DOCUMENTS

| | | | |
|---|---|---|---|
| 6,468,265 B1 | 10/2002 | Evans et al. | |
| 8,108,025 B2 * | 1/2012 | Csavoy .................. | A61B 90/18 600/407 |

(Continued)

*Primary Examiner* — Baisakhi Roy
(74) *Attorney, Agent, or Firm* — Laurence Greenberg; Werner Stemer; Ralph Locher

(57) ABSTRACT

A method for repositioning a mobile imaging system includes:
a) capturing an image recording of at least one optical marker as a reference variable which is disposed close to an examination and/or treatment area of an object,
b) capturing the image recording direction as a further reference variable,
c) wherein the capturing mobile imaging system is in a predefined position and/or alignment suitable for image recording,
d) detecting a changed and/or non-capturable position of the at least one optical marker and/or a changed and/or non-capturable image recording direction, and
e) repositioning the mobile imaging system using a comparison of the reference variables from a) and b) with the respectively corresponding reference variables from d). An image capturing unit and an optical marker are also provided.

13 Claims, 1 Drawing Sheet

(56) References Cited

U.S. PATENT DOCUMENTS

| | | | |
|---|---|---|---|
| 8,141,779 B1* | 3/2012 | Gudenburr | G06K 7/084 235/379 |
| 9,350,914 B1* | 5/2016 | Kaur | H04N 5/23229 |
| 2002/0150215 A1 | 10/2002 | Barnes et al. | |
| 2004/0013240 A1* | 1/2004 | Mitschke | A61B 6/547 378/205 |
| 2009/0076368 A1* | 3/2009 | Balas | A61B 1/00149 600/407 |
| 2009/0310869 A1* | 12/2009 | Thiel | G01B 11/2513 382/201 |
| 2010/0128839 A1* | 5/2010 | Partain | A61N 5/1048 378/4 |
| 2011/0004431 A1* | 1/2011 | Ringholz | A61B 6/4441 702/94 |
| 2011/0250962 A1* | 10/2011 | Feiner | A63F 13/213 463/31 |
| 2013/0006093 A1* | 1/2013 | Raleigh | A61B 5/0037 600/411 |
| 2013/0033700 A1* | 2/2013 | Hallil | G01B 11/00 356/72 |
| 2013/0218024 A1* | 8/2013 | Boctor | A61B 8/4254 600/476 |
| 2015/0257846 A1* | 9/2015 | Kubiak | A61B 6/487 600/407 |

* cited by examiner

METHOD FOR REPOSITIONING A MOBILE IMAGING SYSTEM, IMAGE CAPTURING UNIT AND OPTICAL MARKER

CROSS-REFERENCE TO RELATED APPLICATION

This application claims the priority, under 35 U.S.C. §119, of German Patent Application DE 10 2013 217 476.4, filed Sep. 3, 2013; the prior application is herewith incorporated by reference in its entirety.

BACKGROUND OF THE INVENTION

Field of the Invention

The invention relates to a method for repositioning a mobile imaging system as well as to an image capturing unit and an optical marker.

The invention belongs particularly to the field of medical technology. One field of application is the field of radiology, in which typically computer-aided RIS (radiology information system), HIS (hospital information system), KIS (German term for hospital information system) and PACS (picture archiving and communication system) systems are used. Radiology is based on image acquisition on various modalities or medical imaging systems, such as e.g. a computed tomography scanner (CT), a magnetic resonance imaging scanner (MRI), a positron emission tomography scanner (PET), an X-ray system (X-ray) or an ultrasound system (US). The radiological examination systems present the image data set. The image data set is generally an image volume data set containing a volume image, or an image series data set containing a series of images.

For cost reasons, mobile X-ray systems in the lower price bracket are frequently used, in particular in developing markets.

Within the environment of medical imaging and/or treatment devices such as for example X-ray or C-arm systems, provision may be made for various reasons to at least partially and/or at least approximately determine the position of the patient and/or of other objects, in particular the spatial treatment and/or examination area of the patient. To that end, measuring devices, in particular sensors, are typically used to record measurement data, from which the required boundary information relating to the treatment and/or examination area can be derived. Such boundary information in X-ray devices, which have a C-arm as a movable component, is particularly suitable.

In order to be able to better determine changes in patients between presurgical examinations and surgical treatment, image recordings are produced, ideally on the same table. The position of the medical imaging system can be re-adjusted therewith.

Repositioning of a mobile C-arm system is currently a time-consuming procedure carried out with multiple exposures to X-rays, and the procedure must frequently be carried out during surgery.

Repositioning of the mobile C-arm system is frequently also necessary after acquisition of an X-ray image of the examination or treatment area. After an X-ray image is acquired, the mobile C-arm system is usually pushed away from the operating table into a rest position, only to be pushed back to the operating table for the next necessary image recording. It is necessary in that case for the image recording to cover substantially the same image of the examination or treatment area. Typically, a plurality of X-ray image recordings are taken until the desired image can be detected. That is time-consuming and is carried out with X-ray monitoring.

Various technical approaches are possible to solve the problem of repositioning an imaging system such as the C-arm system:

Motorized driving of the C-arm with position detection.
Use of optical navigation methods.
Optical patterns (usually infrared technology) on the floor of the operating room and a corresponding camera at the housing of the C-arm system.
An electric coil configuration introduced into the floor of the operating room and a dipole transmitting coil at the housing of the C-arm system.
Use of Laser Projection: traditionally a light source, preferably a laser which projects laser markers onto the patient which are verified by using an image recording, is used for visually checking a treatment area in radiology.

Except for the laser sighting system, the other above-mentioned methods are not oriented to the patient, but to external reference systems.

SUMMARY OF THE INVENTION

It is accordingly an object of the invention to provide a method for repositioning a mobile imaging system, an image capturing unit and an optical marker, which overcome the hereinafore-mentioned disadvantages of the heretofore-known methods, units and markers of this general type and which provide improved technology for repositioning a mobile imaging system.

With the foregoing and other objects in view there is provided, in accordance with the invention, a method for repositioning a mobile imaging system, comprising the following steps:

a) capturing an image recording of at least one optical marker as a reference variable which is disposed close to an examination and/or treatment area of an object,
b) capturing the image recording direction as a further reference variable,
c) the capturing mobile imaging system being in a pre-defined position and/or alignment suitable for image recording,
d) detecting a changed and/or non-capturable position of the at least one optical marker and/or a changed and/or non-capturable image recording direction, and
e) repositioning the mobile imaging system using a comparison of the reference variables from a) and b) with the respectively corresponding reference variables from d).

With the objects of the invention in view, there is also provided an image capturing unit for a mobile imaging system for the repositioning thereof, comprising:

a) means for capturing an image recording of at least one optical marker as a reference variable which is disposed close to an examination and/or treatment area of an object,
b) means for capturing the image recording direction as a further reference variable,
c) means for detecting a changed and/or non-capturable position of the at least one optical marker and/or a changed and/or non-capturable image recording direction, and
d) means for outputting notifications relating to the orientation and direction during a repositioning of the mobile imaging system using a comparison of the reference variables from a) and b) with the respectively corresponding reference variables from c).

With the objects of the invention in view, there is concomitantly provided an optical marker suitable for being detected by an image capturing unit according to the invention, which is applied on a sterile cover for covering an object, wherein the optical marker is configured in such a way that it represents defined and, if appropriate, coded boundary information relating to the boundary of an examination and/or treatment area of the object.

The invention has the advantage that repositioning of the imaging system does not depend on registration or reference to an external reference system. However, it does not refer to only the patient either, since the patient can be covered and thus the examination or treatment area would no longer be readily visible. As a result, repositioning is oriented close to the examination or treatment area, which requires little outlay and is cost-effective.

Other features which are considered as characteristic for the invention are set forth in the appended claims.

Although the invention is illustrated and described herein as embodied in a method for repositioning a mobile imaging system, an image capturing unit and an optical marker, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 1:
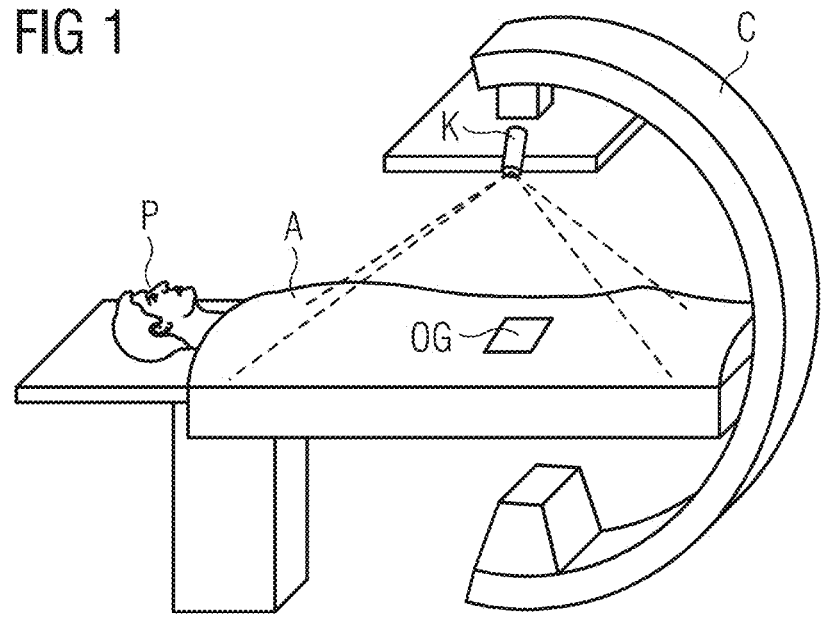
FIG. 1 is a diagrammatic, perspective view of an example of a structure of a medical imaging system.

Referring now to the figures of the drawings in detail and first, particularly, to FIG. 1 thereof, there is seen an example of a structure of a medical imaging system, for example a modern system referred to as a C-arm system, in which the C-arm system can be configured as a mobile system. In that case, non-illustrated rollers are usually located at a housing of the C-arm system so that the latter may be moved back and forth. The invention is, however, not limited thereto. Such a system has at least one X-ray tube or X-ray source with an oppositely located detector, in which the X-ray source and the detector are disposed in such a way that a patient P to be transilluminated using X-rays can be placed between the two. Recording units, the X-ray source and the detector can together be referred to as a recording unit. The patient P is on a displaceable patient couch, bed or table. The patient P is scanned multiple times by moving the C-arm C, during which X rays produced by the X-ray source travel through the patient P and are captured on a detector after passage through the patient.

The imaging system can furthermore have non-illustrated means suitable for carrying out the method according to the invention.

A computer unit frequently serves to control the imaging system. The control, for its part, and the reading of detector output data, take place over a control and data line connecting the computer unit to the recording unit. An operating apparatus, such as a touch screen or panel or a touch keypad for a user, is provided at the computer unit.

FIG. 1 furthermore indicates an examination or treatment area OG of a patient. The patient P is typically covered by a sterile cover A. A kind of viewing window is frequently incorporated in the cover by way of a transparent film, so as not to cover the examination or treatment area. The cover is frequently a green sheet, which is bonded by using adhesive strips at the edges toward the treatment area in such a way that it cannot move out of place.

Furthermore, one or more optical image capturing units K in the form of a camera can be mounted on the C-arm system (on the side of the X-ray source and/or the detector), in which case the recording direction of the camera toward the C-arm system does not need to be registered relatively. Image recordings can be taken in relative direction. The direction of the image recording is a reference variable for obtaining a spatial orientation for the positioning of the C-arm system.

Figure 2:
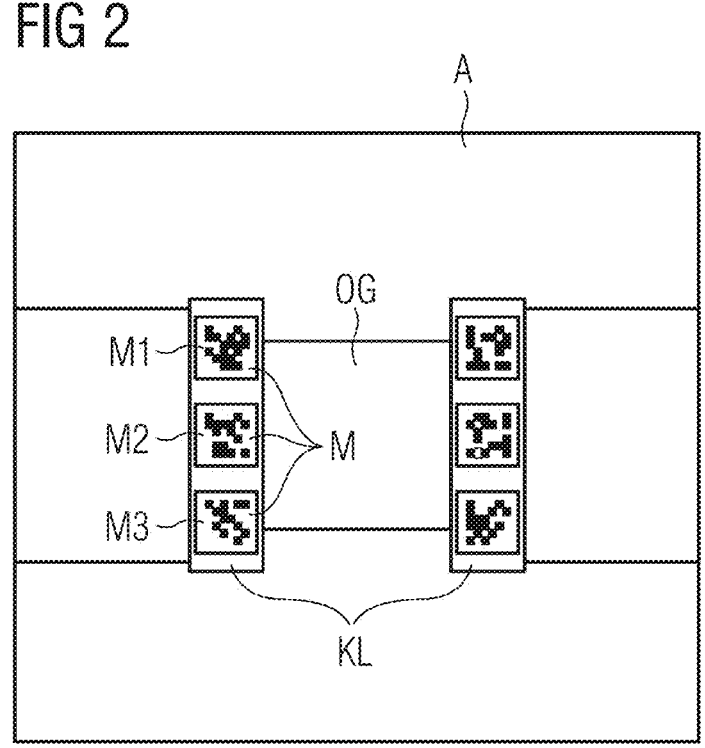
FIG. 2 is a plan view illustrating an application of an optical marker on a sterile cover.

FIG. 2 shows an illustration of applying an optical marker M on a sterile cover A. The optical marker is applied on the sterile cover by using an adhesive or an adhesive strip KL in which the optical marker is incorporated or is applied on the adhesive strip.

The optical marker M can be formed of one or more markers, for example M1, M2, M3 as is indicated in FIG. 2, each of which can contain a pattern. An optical marker M captured by an image capturing unit K is likewise a reference variable with which the C-arm system can be positioned.

Specific boundary information can be contained or encoded in the pattern of the marker, for example by using a barcode or a quick response code. The boundary information is based on the examination or treatment area OG. In this manner, the optical marker is applied close to the examination or treatment area on the cover, without being disposed on the object itself. The marker M thus remains visible even if the object is covered. The cover A can be a green sheet. It is recommended to choose a fabric or a plastic or a color for the cover and for the marker which do not cause irritation during detection of the optical marker.

When the comparison of the corresponding reference variables or of at least one reference variable cannot (or can no longer) be detected or is not (or is no longer) visible or detectable (which is the case if the mobile C-arm system is distanced too far from the examination or treatment area), repositioning of the C-arm system is necessary. In other words, the non-capturable position of the markers or non-capturable image direction are outside the range of the image capturing unit K. In this case, differences in the comparison can provide indications as to the direction in which the C-arm system should be displaced in order to bring it into a position suitable for the image recording or into the original position.

The invention claimed is:

1. A method for repositioning a mobile imaging system, the method comprising the following steps:

a1) placing a cover over an examination or treatment area of an object and applying at least one optical marker to the cover at a location close to the examination or treatment area, wherein the optical marker includes a pattern formed thereon, wherein the pattern is encoded with boundary information relating to a boundary of an examination or treatment area of the object;

a2) capturing an image recording of the at least one optical marker as a reference variable;

b) capturing an image recording direction as a further reference variable;

c) placing the capturing mobile imaging system in at least one of a predefined position or alignment suitable for image recording;

d) detecting at least one of a changed or non-capturable position of the at least one optical marker or at least one of a changed or non-capturable image recording direction; and e) repositioning the mobile imaging system using a comparison of the reference variables from steps a2) and b) with respectively corresponding reference variables from step d).

2. The method according to claim 1, wherein the cover is a sterile cover.

3. The method according to claim 1, which further comprises iteratively repeating the comparison between the reference variables to obtain indications relating to an orientation and direction during repositioning until the mobile imaging system has returned to at least one of the predefined position or alignment suitable for image recording.

4. The method according to claim 1, wherein the cover is a sheet.

5. The method according to claim 1, wherein the pattern encoded with boundary information is a barcode or a quick response code that is formed on the optical marker.

6. A combination comprising:

a cover placed over an examination or treatment area of an object, said cover including at least one optical marker located close to the examination or treatment area of the object, wherein the optical marker includes a pattern formed thereon, wherein the pattern is encoded with boundary information relating to a boundary of an examination or treatment area of the object; and an image capturing unit for repositioning a mobile imaging system, the image capturing unit configured for:

a) capturing an image recording of the at least one optical marker as a reference variable;

b) capturing an image recording direction as a further reference variable;

c) detecting at least one of a changed or non-capturable position of the at least one optical marker or at least one of a changed or non-capturable image recording direction; and d) outputting notifications relating to an orientation and direction during a repositioning of the mobile imaging system using a comparison of the reference variables from a) and b) with respectively corresponding reference variables from c).

7. The combination according to claim 6, wherein the image capturing unit is configured to capture the at least one optical marker having the pattern representing the boundary information relating to a boundary of at least one of the examination or treatment area.

8. The combination according to claim 6, wherein the image capturing unit is configured to detect the at least one optical marker applied on a sterile cover of the object.

9. An optical marker suitable to be detected by an image capturing unit according to claim 6 and applied on a sterile cover for covering an object, the optical marker comprising:

an optical marker including a pattern formed thereon, wherein the pattern is encoded with boundary information relating to a boundary of an examination or treatment area of the object, wherein the cover is a sheet.

10. The optical marker according to claim 9, which further comprises an adhesive or adhesive strip in which the optical marker is incorporated or on which the marker is applied, said adhesive or adhesive strip applying the optical marker on the sterile cover.

11. The optical marker according to claim 9, wherein the pattern encoded with boundary information is a barcode or a quick response code that is formed on the optical marker.

12. The combination according to claim 6, wherein the cover is a sheet.

13. The combination according to claim 6, wherein the pattern encoded with boundary information is a barcode or a quick response code that is formed on the optical marker.

* * * * *